(12) United States Patent
Santori et al.

(10) Patent No.: US 8,593,629 B2
(45) Date of Patent: Nov. 26, 2013

(54) APPARATUS FOR PERFORMING SERS

(75) Inventors: Charles M. Santori, Palo Alto, CA (US); Kai-Mei Camilla Fu, Palo Alto, CA (US); Marco Fiorentino, Mountain View, CA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 158 days.

(21) Appl. No.: 13/029,915

(22) Filed: Feb. 17, 2011

(65) Prior Publication Data

US 2012/0212732 A1    Aug. 23, 2012

(51) Int. Cl.
*G01J 3/44*    (2006.01)

(52) U.S. Cl.
USPC .......................................... 356/301; 436/164

(58) Field of Classification Search
USPC ................... 356/301–344; 977/954; 436/164
See application file for complete search history.

(56) References Cited

U.S. PATENT DOCUMENTS

| | | | |
|---|---|---|---|
| 5,677,196 A * | 10/1997 | Herron et al. ................. | 436/518 |
| 6,193,870 B1 | 2/2001 | Morse et al. | |
| 6,222,619 B1 * | 4/2001 | Herron et al. .................... | 356/39 |
| 6,756,795 B2 | 6/2004 | Hunt et al. | |
| 6,777,244 B2 | 8/2004 | Pepper et al. | |
| 7,256,886 B2 | 8/2007 | Cullum et al. | |
| 7,342,656 B2 | 3/2008 | Islam et al. | |
| 7,463,661 B2 * | 12/2008 | Ogura ......................... | 372/44.01 |
| 7,528,948 B2 * | 5/2009 | Bratkovski et al. ........... | 356/301 |
| 7,583,379 B2 | 9/2009 | Zhao et al. | |
| 7,656,525 B2 | 2/2010 | Zhao et al. | |
| 7,667,238 B2 | 2/2010 | Erchak | |
| 7,833,842 B2 | 11/2010 | Williams | |
| 2003/0077023 A1 * | 4/2003 | Troll ................................ | 385/16 |
| 2006/0038990 A1 * | 2/2006 | Habib et al. .................. | 356/301 |
| 2006/0231381 A1 | 10/2006 | Jensen et al. | |
| 2007/0070341 A1 | 3/2007 | Wang et al. | |
| 2007/0252136 A1 | 11/2007 | Lieber et al. | |

(Continued)

FOREIGN PATENT DOCUMENTS

| | | |
|---|---|---|
| EP | 2058908 A1 | 5/2009 |
| JP | 2000-206048 | 7/2000 |
| WO | WO-2010088585 | 8/2010 |
| WO | WO-2010126640 | 11/2010 |

OTHER PUBLICATIONS

Gopinath, Ashwin, et al., Deterministic Aperiodic Arrays of Metal Nanoparticles for Surface-enhanced Raman Scattering (SERS), Publication Date: Mar. 2, 2009; vol. 17; On pp. 3741-3753. < http://www.bio-page.org/boriskina/Boriskina_OE2009.pdf >.

(Continued)

*Primary Examiner* — Gregory J Toatley
*Assistant Examiner* — Dominic J Bologna (57) ABSTRACT

An apparatus for performing surface enhanced Raman spectroscopy includes an optical waveguide, a plurality of flexible nano-structures, wherein the plurality of nano-structures have respective free ends positioned within an evanescent field to be generated by light propagated through the optical waveguide, wherein the plurality of nano-structures are movable from a first position and a second position, wherein in the first position, the free ends of the plurality of nano-structures are substantially spaced from each other and in the second position, the free ends of a plurality of the nano-structures are substantially in contact with each other.

12 Claims, 7 Drawing Sheets

(56) References Cited

U.S. PATENT DOCUMENTS

| | | |
|---|---|---|
| 2008/0017845 A1 | 1/2008 | Drndic et al. |
| 2008/0024776 A1 | 1/2008 | Bratkovski et al. |
| 2008/0098805 A1 | 5/2008 | Jin et al. |
| 2008/0144026 A1* | 6/2008 | Zhao et al. ............... 356/301 |
| 2008/0166706 A1* | 7/2008 | Zhang et al. ................ 435/6 |
| 2008/0174775 A1 | 7/2008 | Moskovits et al. |
| 2008/0187648 A1 | 8/2008 | Hart et al. |
| 2008/0311028 A1 | 12/2008 | Stanbery |
| 2009/0261815 A1 | 10/2009 | Cairns et al. |
| 2009/0303472 A1 | 12/2009 | Zhao et al. |
| 2011/0001118 A1 | 1/2011 | Bhupendra |
| 2011/0030792 A1 | 2/2011 | Miguez |
| 2011/0116089 A1 | 5/2011 | Schmidt et al. |
| 2011/0128537 A1* | 6/2011 | Bond et al. ............... 356/301 |
| 2012/0107948 A1* | 5/2012 | Li et al. ................... 436/149 |

OTHER PUBLICATIONS

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol. 20; On pp. 3533-3538. < http://onlinelibrary.wiley.com/doi/10.1002/adma.200702478/abstract >.

Josef Giglmayr, "Nano-Finger Electrodes for the Electro-Optical Generation and Tuning of Gratings at Several Wavelengths", <http://www.ipme.ru/ipme/conf/NN2003/NN2003_Abstracts.pdf > Publication Date: Aug. 30, 2003-Sep. 6, 2003.

Baldwin, Jean, Norbert Schuhler, Ian S. Butler, & Mark P. Andrews, "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Fan et al., "Multilayer Silver Nanoparticles Modified Optical Fiber Tip for High Performance SERS Remote Sensing," 217th ECS Meeting—Vancouver, Canada, Apr. 25-Apr. 30, 2010, J2—Electrochemical Nano/Bio Sensors 2, Abs# 1830.

Fan, J. G. et al., "Integrating Aligned Nanorod Array onto Optical Fibers for SERS Probes," Proc. of SPIE—Nanoengineering: Fabrication, Properties, Optics, and Devices III, vol. 6327, 2006, pp. R-1 to R10.

Guieu, Valérie, et al. "Multitip-localized enhanced Raman scattering from a nanostructured optical fiber array." The Journal of Physical Chemistry C 113.3 (2008): 874-881.

International Search Report, Mar. 30, 2011, PCT Application No. PCT/US2010/044039, Filed Jul. 30, 2010.

Lucotti et al., "Fiber-optic SERS sensor with optimized geometry," Elsevier, ScienceDirect, Sensors and Actuators B, vol. 121, 2007, 356-364.

PCT International Search Report, Jan. 20, 2011, Hewlett-Packard Development Company, L.P. (PCT/US2010/031790, Filed Apr. 20, 2010).

PCT International Search Report, Dec. 23, 2010, Hewlett-Packard development Company, L.P. (PCT/US2010/031809, Filed Apr. 20, 2010).

Ren, Hongliang, et al. "The preparation of optical fibre nanoprobe and its application in spectral detection." Optics & Laser Technology 39.5 (2007): 1025-1029.

Segawa, H., et al., "Top-gathering pillar array of hybrid organic-inorganic material by means of self-organization", Applied Physics A—Materials Science & Processing, Mar. 17, 2006, vol. 83, pp. 447-451.

White, Daniel J., et al. "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

* cited by examiner

FIG. 10

APPARATUS FOR PERFORMING SERS

CROSS-REFERENCE TO RELATED APPLICATION

The present application contains some common subject matter with copending and commonly assigned U.S. patent application Ser. No. 12/905,891, filed on Oct. 15, 2010, by Wei Wu et al., the disclosure of which is hereby incorporated by reference in its entirety.

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman scattering.

Raman scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

Unfortunately, the signal produced by Raman scattering is extremely weak in many instances compared to elastic or Rayleigh scattering from an analyte species. The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Disclosed herein are a method and apparatus for performing surface enhanced Raman spectroscopy (SERS) to detect a molecule in an analyte sample with a relatively high level of sensitivity. The apparatus includes an optical waveguide through which light is to be propagated to generate evanescent waves. The apparatus also includes a plurality of flexible nano-structures having respective free ends that are positioned to be within the evanescent waves generated from the light propagating through the optical waveguide. The nano-structures are movable from a first position in which the free ends of the nano-structures are substantially spaced from each other and a second position in which the free ends of the nano-structures are substantially in contact with each other. The free ends that substantially contact each other form hot spots of relatively higher electrical energy that substantially enhance production of Raman-scattered light from analyte molecules positioned at or near the free ends. In this regard, as the free ends of multiple nano-structures move to be in substantial contact with each other, an analyte molecule may become trapped between the free ends and may thus be held within a hot spot to thereby enable enhanced Raman scattered light emission from the analyte molecule.

Through implementation of the apparatus and method disclosed herein, a SERS system that implements the apparatus may include fiber coupling. More particularly, for instance, an optical fiber may be directly coupled to the optical waveguide and excitation light may be emitted into the optical waveguide through the optical fiber. In one regard, the coupling of optical fibers to the optical waveguide is simpler than coupling free-space signals to optical fibers or the optical waveguide and may result in relatively smaller devices. In another regard, the coupling of optical fibers to the optical waveguide generally results in a reduction of required laser power as compared with free-space coupling. Moreover, the signal collected from each waveguide is in a single optical mode and may thus allow for more efficient spectroscopy as compared with free-space coupled waveguides.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultraviolet portions of the electromagnetic spectrum.

Figure 1A:
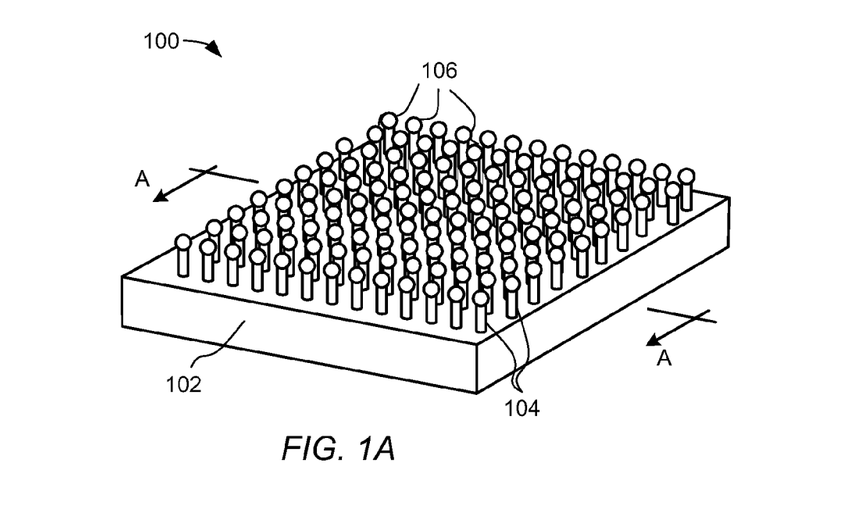
FIG. 1A shows an isometric view of an apparatus for performing SERS, according to an example of the present disclosure.

FIG. 1A shows an isometric view of an apparatus 100 for performing SERS, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

The apparatus 100 is operable to perform SERS to detect a molecule in an analyte sample with a relatively high level of sensitivity. The apparatus 100 includes an optical waveguide 102 and a plurality of nano-structures 104, in this example, nano-fingers. More particularly, the nano-fingers 104 are depicted as being attached to and extending above a surface of the optical waveguide 102. The nano-fingers 104 may be attached to the surface of the optical waveguide 102 through any suitable attachment mechanism. For instance, the nano-fingers 104 may be grown directly on the optical waveguide 102 surface through use of various suitable nano-structure growing techniques. As another example, the nano-fingers 104 may be integrally formed with the optical waveguide 102. In this example, for instance, a portion of the material from which the optical waveguide 102 is fabricated may be etched or otherwise processed to form the nano-fingers 104. In a further example, a separate layer of material may be adhered to the optical waveguide 102 surface and the separate layer of material may be etched or otherwise processed to form the nano-fingers 104.

The nano-fingers 104 are formed of a relatively flexible material to enable the nano-fingers 104 to be laterally bendable, for instance, to enable free ends 106 of the nano-fingers 104 to move toward each other, as discussed in greater detail herein below. Examples of suitable materials for the nano-fingers 104 include polymer materials, such as, polydimethylsiloxane (PDMS) elastomer, polyimide, polyethylene, polypropelene, etc., metallic materials, such as, gold, silver, aluminum, etc., semiconductor materials, etc. In various examples, the nano-fingers 104 may be fabricated through a nanoimprinting process in which a template of relatively rigid pillars is employed in a multi-step imprinting process on a polymer matrix to form the nano-fingers 104. Various other processes, such as, etching, and various techniques used in the fabrication of micro-electromechanical systems (MEMS) and nano-electromechanical systems (NEMS) may also be used to fabricate the nano-fingers 104.

A nano-finger 104 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 104 laterally onto one or more neighboring nano-fingers 104. In some examples, the length exceeds the cross sectional dimension (or width) by more than a factor of about 5 or 10. For example, the width may be about 100 nanometers (nm) and the height may be about 500 nm. In another example, the width at the base of the nano-finger 104 may range between about 20 nm and about 300 nm and the length may be more than about 1 micrometer (μm). In other examples, the nano-finger 104 is sized based upon the types of materials used to form the nano-finger 104. Thus, for instance, the more rigid the material(s) used to form the nano-finger 104, the less the width of the nano-finger 104 may be to enable the nano-finger 104 to be laterally collapsible. In further examples the nano-fingers may form ridges in which two of three dimensions (for instance length and height) exceed by more than several times a nanoscale cross sectional dimension (for instance, width). According to a particular example, and as discussed in greater detail herein below, the nano-fingers 104 have heights that position their free ends 106 within an evanescent field to be generated by electromagnetic radiation propagated through the optical waveguide 102. More particularly, the nano-fingers 104 have heights that position their free ends 106 to be within an evanescent field that is of sufficient strength to cause detectable Raman scattered light to be emitted by analyte molecules positioned on or near the free ends 106.

As shown in FIG. 1A, the nano-fingers 104 are arranged in an array on the optical waveguide 102. The array may include a substantially random distribution of nano-fingers 104 or a predetermined configuration of nano-fingers 104. In any regard, and as discussed in greater detail herein below, the nano-fingers 104 are arranged with respect to each other such that the free ends 106 of at least two neighboring nano-fingers 104 are able to touch each other when the nano-fingers 104 are in a bent condition. By way of particular example, the neighboring nano-fingers 104 are positioned less than about 100 nanometers apart from each other. In addition, although FIG. 1A depicts the array as having a relatively large number of nano-fingers 104 arranged along each row, it should be understood that the array may include any number of nano-fingers 104 in each row without departing from a scope of the apparatus 100. In one regard, the apparatus 100 may include a relatively large number of nano-fingers 104 to enhance the likelihood of capturing analyte molecules to be detected between the free ends 106 of multiple nano-fingers 104.

The nano-fingers 104 have been depicted in FIG. 1A as having substantially cylindrical cross-sections. It should, however, be understood that the nano-fingers 104 may have other shaped cross-sections, such as, for instance, rectangular, square, triangular, etc. In addition, or alternatively, the nano-fingers 104 may be formed with one or more features, such as, notches, bulges, etc., to substantially cause the nano-fingers 104 to be inclined to bend in a particular direction. Thus, for instance, two or more adjacent nano-fingers 104 may include the one or more features to increase the likelihood of the free ends 106 of these nano-fingers 104 to bend toward each other.

The optical waveguide 102 is a structure that is operable to guide electromagnetic waves in the optical spectrum. In this regard, the optical waveguide 102 may be formed of an optically transparent material, such as, glass, plastic, polymer, etc. The optical waveguide 102 may also be formed of a fluid material, such as, water or other transparent or substantially transparent material, as discussed in greater detail herein below.

Figure 1B:
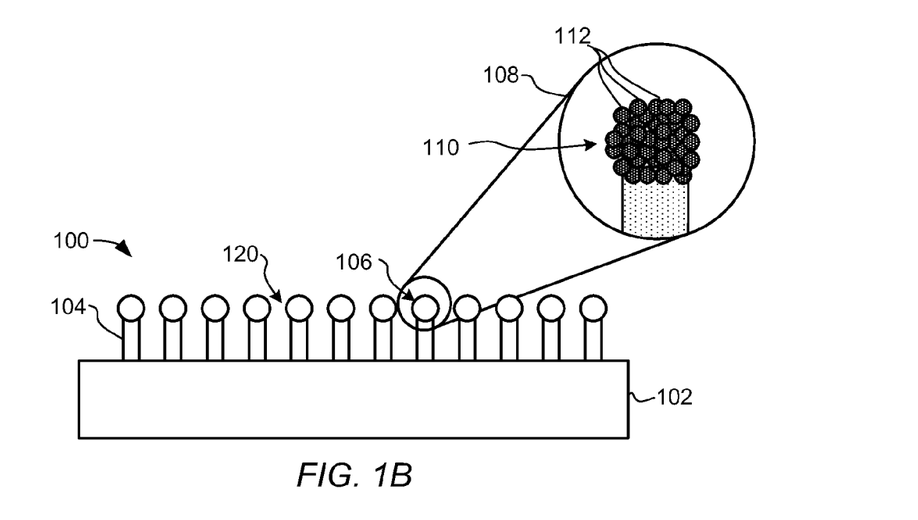
FIGS. 1B and 1C show cross-sectional views along a line A-A, shown in FIG. 1A of the apparatus, according to examples of the invention.

Turning now to FIG. 1B, there is shown a cross-sectional view along a line A-A, shown in FIG. 1A, of the apparatus 100, in accordance with an example. In addition, a free end 106 of a nano-finger 104 is magnified in an enlargement 108, which reveals that the nano-finger 104 may include an active material layer 110 disposed on the outer surface, near the tip or free end 106, of the nano-finger 104. According to one or more examples, the active material layer 110 comprises a SERS-active material, such as, the SERS-active nano-particles 112 depicted in FIG. 1B. According to other examples, the active material layer 110 comprises a separate layer, for instance, positioned underneath the nano-particles 112 depicted in FIG. 1B. In these examples, the active material layer 110 may be fabricated as part of and integrated with the nano-finger 104. In other examples, for instance, in which the nano-fingers 104 are formed of a metallic material, the active material layer 110 may be omitted since the nano-fingers 104 themselves may be the SERS-active material.

The other nano-fingers 104 may also include the active material layer 110/SERS-active nano-particles 112 as represented by the circles on the tops or free ends of the nano-fingers 104. Although the enlargement 108 depicts the nano-particles 112 as covering the entire tip of the nano-finger 104, it should be understood that examples of the apparatus 100 may be implemented with gaps between some of the nano-particles 112. It should also be noted that examples of the apparatus 100 are not limited to nano-particles 112 disposed over just the tips of the nano-scale protrusions 104. In other examples, the nano-particles 112 may be disposed over part of or nearly the entire surface of the nano-fingers 104. In any regard, the SERs-active nano-particles 112 may be deposited onto at least the free ends of the nano-fingers 104 through, for instance, physical vapor deposition (PVD), chemical vapor deposition (CVD), sputtering, etc., of metallic material, or self-assembly of pre-synthesized nano-particles. By way of example, the angle at which the nano-particles 112 are deposited onto the free second ends of the nano-fingers 104 may be controlled to thereby substantially control the deposition of the nano-particles 112.

In addition, the active material layer 110/nano-particles 112 may one or both of enhance Raman scattering and facilitate analyte adsorption. For instance, the active material layer 110/nano-particles 112 may comprise a Raman-active material such as, but not limited to, gold (Au), silver (Ag), and copper (Cu) having nanoscale surface roughness. Nanoscale surface roughness is generally characterized by nanoscale surface features on the surface of the layer(s) and may be produced spontaneously during deposition of the Raman-active material layer(s). By definition herein, a Raman-active material is a material that facilitates Raman scattering and the production or emission of the Raman signal from an analyte adsorbed on or in a surface layer or the material during Raman spectroscopy.

In some examples, the active material layer 110/nano-particles 112 may be annealed or otherwise treated to increase nanoscale surface roughness of the active material layer 110/nano-particles 112 after deposition. Increasing the surface roughness may enhance Raman scattering from an adsorbed analyte, for example. Alternatively, the arrangement of the nano-particles 112 may provide a nanoscale roughness that enhances Raman scattering, for example.

In some examples, a surface of the nano-fingers 104 may be functionalized to facilitate adsorption of the analyte. For example, the tips or free ends of the nano-fingers 104 in a vicinity thereof (not illustrated) may be functionalized with a binding group to facilitate binding with a specific target analyte species. A surface of the active material layer 110/nano-particles 112 may be functionalized, for example. The functionalized surface (that is, either a surface of the nano-finger 104 itself, the active material layer 110/nano-particles 112, or both) may provide a surface to which a particular class of analytes is attracted and may bond or be preferentially adsorbed. The functionalized surface may selectively bond with protein, DNA or RNA, for example.

Although the nano-fingers 104 have been depicted in FIGS. 1A-1B as each extending vertically and at the same heights with respect to each other, it should be understood that some or all of the nano-fingers 104 may extend at various angles and heights with respect to each other. The differences in angles and/or heights between the nano-fingers 104 may be based upon, for instance, differences arising from manufacturing or growth variances existent in the fabrication of the nano-fingers 104 and the deposition of the nano-particles 112 on the nano-fingers 104, etc.

As shown in FIG. 1B, the nano-fingers 104 are in a first position, in which the free ends 106 are in a substantially spaced arrangement with respect to each other. The gaps 120 between the free ends 106 may be of sufficiently large size to enable analyte or other liquid to be positioned in the gaps 120. In addition, the gaps 120 may be of sufficiently small size to enable the free ends 106 of at least some of the nano-fingers 104 to move toward each other as the analyte or other liquid evaporates, through, for instance, capillary forces applied on the free ends 106 as the analyte or other liquid dries.

Figure 1C:
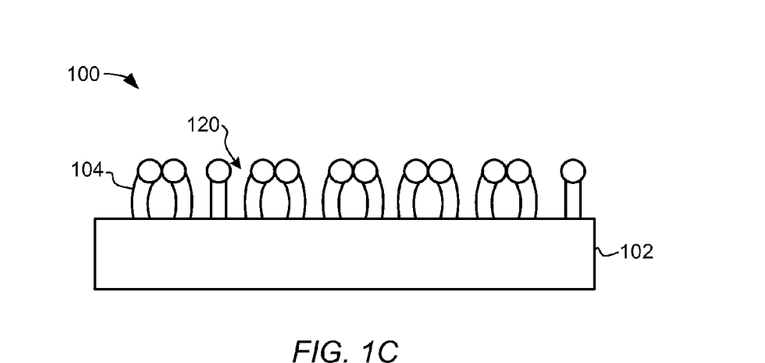

Turning now to FIG. 1C, there is shown a cross-sectional view along a line A-A, shown in FIG. 1A, of the apparatus 100, in accordance with another example. The view depicted in FIG. 1C is identical to the view depicted in FIG. 1B, except that the nano-fingers 104 are depicted in a second position, in which the free ends 106 of some of the nano-fingers 104 are in substantial contact with each other. According to an example, the free ends 106 of some of the nano-fingers 104 may be in and may remain in substantial contact with each other for a period of time due to the capillary forces applied on the free ends 106 during and following evaporation of a liquid in the gaps 120 between the free ends 106. In other examples, the free ends 106 of some of the nano-fingers 104 may be maintained in the second positions through, for instance, removal of an electrostatic charge on the free ends 106 as described in the U.S. Ser. No. 12/905,891 application for patent. In those examples, the nano-fingers 104 may be fabricated to normally have the second position depicted in FIG. 1C and may have the first position depicted in FIG. 1B when the electrostatic charge is applied onto the free ends 106 of the nano-fingers 104.

In any event, and in one regard, the free ends 106 of the nano-fingers 104 may be caused to contact each other as shown in FIG. 1C to cause an analyte molecule to be tested to substantially be trapped between contacting free ends 106. By substantially trapping an analyte molecule to be tested between the free ends 106, SERS on the analyte molecule may be enhanced because the relatively small gaps between the free ends 106 create "hot spots" having relatively large electric field strengths. Substantially trapping an analyte molecule here is intended to indicate that the analyte molecule may either be trapped between two free ends 106 or may be attached on one of the free ends 106 of adjacently located free ends 106.

Figure 2:
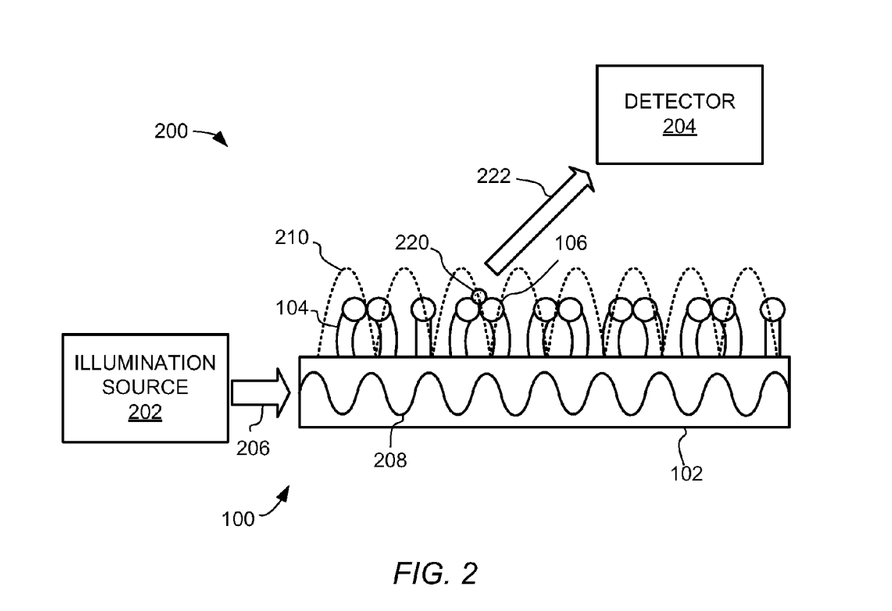
FIG. 2 shows a block diagram of a SERS system employing the apparatus depicted in FIGS. 1A-1C, according to an example of the present disclosure.

With reference now to FIG. 2, there is shown a block diagram of a surface enhanced Raman spectroscopy (SERS) system 200 employing the apparatus depicted in FIGS. 1A-1C, according to an example. It should be understood that the system 200 depicted in FIG. 2 may include additional components and that some of the components described herein may be removed and/or modified without departing from a scope of the system 200. It should also be understood that the components depicted in FIG. 2 are not drawn to scale and thus, the components may have different relative sizes with respect to each other than as shown therein.

As shown in FIG. 2, the SERS system 200 includes the apparatus 100 depicted in FIGS. 1A-1C, an illumination source 202 and a detector 204. In addition, similarly to the view depicted in FIG. 1C, the nano-fingers 104 are illustrated as being in the second position, in which some of the free ends 106 of the nano-fingers 104 are in contact with each other. Moreover an analyte molecule 220 upon which SERS is to be performed is also depicted as being positioned between two of the substantially contacting free ends 106.

The illumination source 202 is depicted as emitting electromagnetic radiation, as represented by the arrow 206, which may comprise, for instance, light, into the optical waveguide 102. By way of example, the illumination source 202 may comprise a laser that supplies the optical waveguide 102 with visible light. In addition, the illumination source 202 may be directly coupled to the optical waveguide 102 through an optical fiber (not shown). The electromagnetic radiation (or excitation light) 206 propagates through the optical waveguide 102 as a wave 208. As the wave 208 propagates through the optical waveguide 102, evanescent waves 210 are generated. More particularly, for instance, the evanescent waves 210 are generated by the wave 208 because the wave 208 strikes the interior walls of the optical waveguide 102 at angles greater than the so-called critical angle. The area above the optical waveguide 102 in which the evanescent waves 210 are emitted is defined herein as the evanescent field. According to an example, the electromagnetic radiation 206 is polarized vertically (TM-polarized) prior to being emitted into the optical waveguide 102 to enhance evanescent wave 210 generation toward the free ends 106 of the nano-fingers 104.

As further depicted in FIG. 2, the free ends 106 of the nano-fingers 104 are positioned within the evanescent field generated by the evanescent waves 210. Generally speaking, the evanescent waves 210 illuminate the free ends 106 (or the active material layer 110/nano-particles 112 provided on the free ends 106), thereby causing hot spots of relatively large electric field strength. The evanescent waves 210 also cause analyte molecules 220 contained in the hot spots to emit detectable Raman light similar to other types of illumination, such as, laser light. These hot spots are increased at the locations where the free ends 106 of multiple nano-fingers 104 contact each other. The electric fields generated at the contact locations between the free ends 106 of the nano-fingers 104 generally enhance the rate at which Raman light is scattered by an analyte molecule 220 positioned at or near the contact locations. The Raman scattered light, which is represented by the arrow 222, is shifted in frequency by an amount that is characteristic of particular vibrational modes of the analyte molecule 220. The detector 204 is to collect the Raman scattered light 222 and spectral analysis may be performed on the Raman scattered light 222 to identify the analyte molecule 220.

The nano-particles 112 located near or adjacent to the analyte molecule(s) 220 may enhance the production of Raman scattered light 222 from the analyte molecule(s) 220 by concentrating or otherwise enhancing an electromagnetic field in a vicinity of the analyte molecule(s) 220. In examples where the nano-fingers 104 are formed of a metallic material, the nano-fingers 104 themselves may also enhance the production of the Raman scattered light 222. As also discussed above, the contacting of two or more of the free ends 106 with each other to trap the analyte molecule(s) 220 may substantially increase the likelihood that the analyte molecule(s) 220 will be positioned near or in contact with some nano-particles 112 and thus be positioned within a hot spot. In this regard, the likelihood that an analyte molecule(s) 220 will produce sufficiently strong Raman scattered light 222 to be detected by the detector 204 will thus also be increased.

Although the Raman scattered light 222 has been depicted as being directed toward the detector 204, the Raman scattered light 222 is emitted in multiple directions. In this regard, some of the Raman scattered light 222 may be directed into the optical waveguide 102. More particularly, for instance, Raman scattered light 222 may be generated in the optical waveguide 102 as a result of the analyte molecule 220 coupling to the evanescent field of a waveguide mode. In these instances, the detector 204 may be positioned to detect the waves generated in the optical waveguide 102 from the Raman scattered light 222. In any regard, the detector 204 may include a filter to filter out light originating from the illumination source 202, for instance, through use of a grating-based monochrometer or interference filters.

The detector 204 is generally to convert the Raman scattered light 222 emitted from the analyte molecule(s) 220 into electrical signals that may be processed to identify, for instance, the analyte molecule 220 type. In some examples, the detector 204 is to output the electrical signals to other components (not shown) configured to process the electrical signals. In other examples, the detector 204 is equipped with processing capabilities to identify the analyte molecule 220 type.

According to an example, the SERS system 200 comprises a system that is integrated on a single chip. For example, the output of the optical waveguide 102 may be connected to an arrayed waveguide grating (AWG filter). The optical waveguide 102 may also be directly coupled to optical fibers in the SERS system 200 through which the illumination light 206 may be supplied and through which the Raman scattered light 222 may be outputted. In this example, the SERS system 200 provides a relatively more compact solution than coupling free-space signals to fibers. Additionally, the SERS system 200 may be implemented efficiently for a relatively large sensing area for which the free-space signals are substantially more complex and/or expensive to implement. The optical waveguide 102 in the SERS system 200 may also be directly coupled to optical fibers in particular instances to form compact field sensors. In this instance the illumination source 202, for instance an excitation laser, and the detector 204, for instance spectral analysis equipment may then be housed in a remote location.

In addition, the Raman scattered light 222 may be collected into a single optical mode for each optical waveguide 102, which generally allows for more efficient spectroscopy. The Raman scattered light 222 from the optical waveguide 102 may then be imaged onto a narrow slit. By contrast, in instances using conventional free-space optics, light collected from a large area cannot be imaged onto a narrow slit, and the device either requires a substantially large optical system or provides low throughput.

With reference now to FIGS. 3-8, there are respectively shown isometric views of portions of apparatuses 300-800 for performing SERS, according to various examples of the present disclosure. The apparatuses 300-800 are particular applications of the apparatus 100 depicted in FIGS. 1A-2 and thus share some common features with the apparatus 100. In this regard, any of the apparatuses 300-800 may be substituted for the apparatus 100 in the SERS system 200. It should be understood that the apparatuses 300-800 depicted in FIGS. 3-8 may include additional components and that some of the components described herein may be removed and/or modified without departing from the scopes of the apparatuses 300-800. It should also be understood that the components depicted in FIGS. 3-8 are not drawn to scale and thus, the components may have different relative sizes with respect to each other than as shown therein.

Generally speaking, each of the apparatuses 300-800 comprises nano-structures 104 that are movable between a first position and a second position as discussed above with respect to the nano-fingers 104. In this regard, the nano-structures 104 in the apparatuses 300-800 comprise any of the materials discussed above with respect to the nano-fingers 104. In addition, the nano-structures 104 in the apparatuses 300-800 may be fabricated in any of the manners discussed above with respect to the nano-fingers 104 to generally enable the nano-structures 104 to be movable from the first position to the second position or vice versa.

As discussed above, in the first position, the free ends of the nano-structures 104 are substantially spaced apart from each other to enable an analyte molecule to be introduced between at least two of the free ends 106. In the second position, the free ends 106 of the nano-structures 104 are substantially in contact with each other. In other words, in the second position, the free ends 106 of at least two of the nano-structures 104 are sufficiently close to each other to substantially trap an analyte molecule 220 between the free ends 106. In addition, each of the nano-structures 104 has been depicted as being in the second positions in the apparatuses 300-800. It should be understood that the nano-structures 104 may initially have been in the first position to enable trapping of an analyte molecule between the free ends 106 of at least two of the nano-structures 104.

Figure 3:
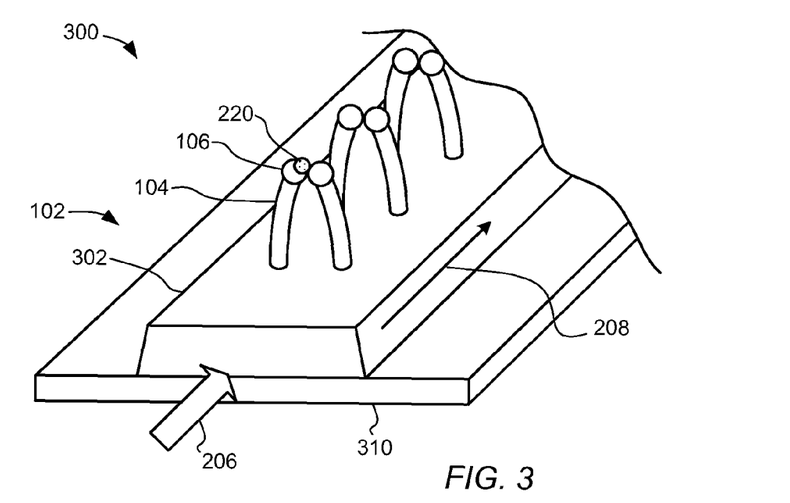
FIGS. 3-8 show respective isometric views of apparatuses for performing SERS, according to various examples of the present disclosure.

With reference first to FIG. 3, the apparatus 300 includes an optical waveguide 102 and a plurality of nano-structures 104, in this example, nano-fingers. The optical waveguide 102 comprises a ridge waveguide 302 positioned on a substrate 310. More particularly, the nano-fingers 104 are depicted as being positioned on top of the ridge waveguide 302. The ridge waveguide 302 generally operates to propagate light waves 208 introduced into the ridge waveguide 302 as discussed above with respect to the optical waveguide 102 in FIG. 2. In this regard, the ridge waveguide 302 may comprise any of the materials discussed above with respect to the optical waveguide 102. In addition, the substrate 310 may be fabricated of any suitable material having sufficient ability to support the ridge waveguide 302 and may have a relatively lower refractive index than the ridge waveguide 302. Similarly to the optical waveguide 102, the light waves 208 may be polarized, are substantially confined within the ridge waveguide 302, and generate evanescent waves 210 (not shown) that may be emitted onto an analyte molecule 220 located on or between the second ends 106 of at least two nano-fingers 104. As discussed above with respect to FIG. 2, the evanescent waves 210 may cause Raman scattered light to be emitted from the analyte molecule 220. In addition, the emission of the Raman scattered light from the analyte molecule 220 may be enhanced through use of the active material layer 110/nano-particles 112 provided on the free ends 106 or by the material forming the nano-fingers 104 themselves. Moreover, the ridge waveguide 302 may be implemented in the collection of the Raman scattered light emitted from the analyte molecule 220 as discussed above.

Figure 4:
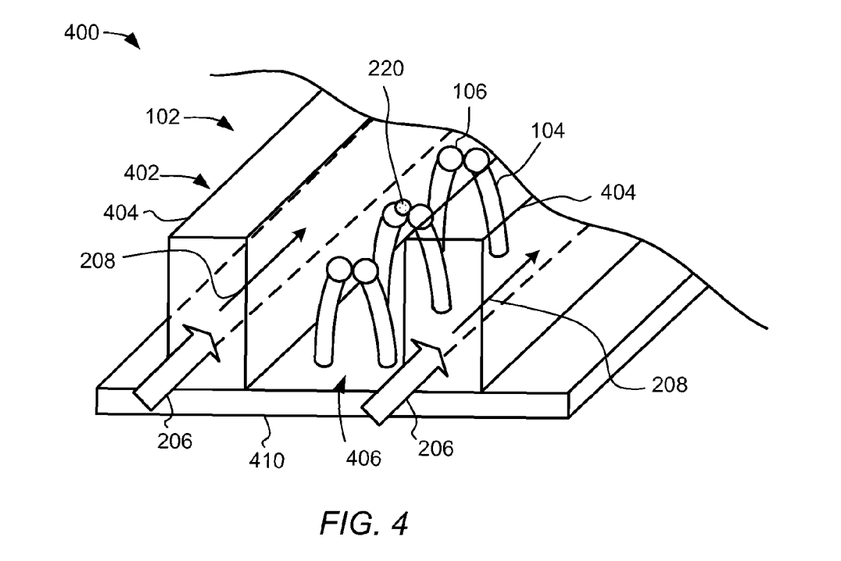

With reference now to FIG. 4, the apparatus 400 includes an optical waveguide 102 and a plurality of nano-structures 104, in this example, nano-fingers. The optical waveguide 102 comprises a slot waveguide 402 formed of a pair of parallel ridges 404 with a slot 406 therebetween. The nano-fingers 104 are depicted as being positioned within the slot 406. Each of the parallel ridges 404 comprises an optical waveguide through which electromagnetic radiation 206, for instance, in the form of light, may be propagated as illustrated by the arrows 208. The electromagnetic radiation 206 may be polarized horizontally (TE-polarized) to enhance generation of evanescent waves (not shown) from light waves 208 propagating through the ridges 404. The width of the slot 406 may be sufficiently small relative to the wavelength of the excitation light 206 to cause the electric field in the gap 406 to be relatively large, for instance, with respect to the electric field within the ridges 404, due to the boundary conditions of the ridges 404. In addition, the free ends 106 of the nano-fingers 104 may be positioned within the evanescent waves, such that, the evanescent waves may cause Raman scattered light to be emitted from an analyte molecule 220 located on or near the free ends 106 of the nano-fingers 104. In addition, the emission of the Raman scattered light from the analyte molecule 220 may be enhanced through use of the active material layer 110/nano-particles 112 provided on the free ends 106 or by the material forming the nano-fingers 104 themselves. Moreover, the ridges 404 may be implemented in the collection of the Raman scattered light emitted from the analyte molecule 220 as discussed above.

As also shown in FIG. 4, the ridges 404 and the nano-fingers 104 are supported on a substrate 410. The substrate 410 may be fabricated of any suitable material having sufficient ability to support the ridges 404 and may have a relatively lower refractive index than the ridges 404.

Figure 5:
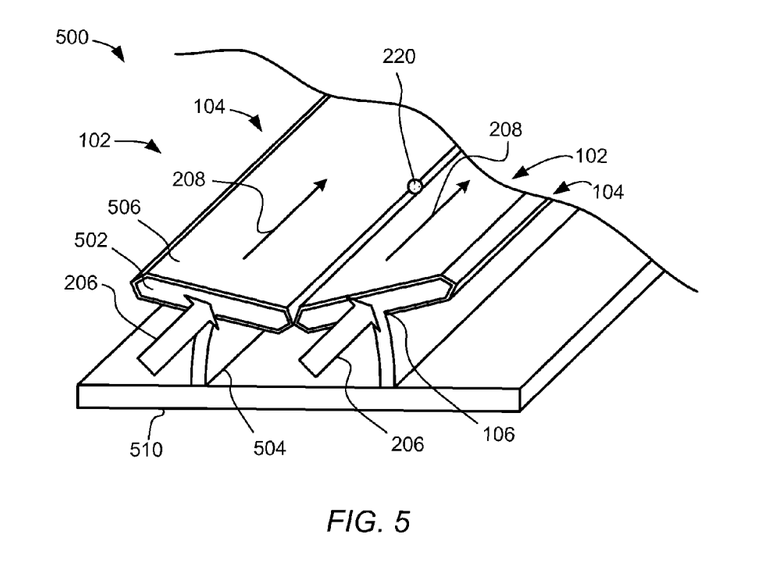

With reference now to FIG. 5, the apparatus 500 includes optical waveguides 102 and nano-structures 104 supported on a substrate 510, which may be equivalent to any of the substrates discussed above. The apparatus 500 differs, however, from the previously described apparatuses 100, 300, and 400, in that the optical waveguides 102 are integrated into respective nano-structures 104. More particularly, the nano-structures 104 comprise a ridge section 502 supported on a free end 106 of the nano-structures 104. The ridge section 502 may be formed of the same materials as those discussed above with respect to the optical waveguide 102 to thereby enable excitation light 206 to propagate therethrough. In addition, the base section 504 may be formed of the same materials as those discussed above with respect to the nano-fingers 104. In one example, the base section 504 and the ridge section 502 may be formed as an integrated component using any of the fabrication techniques discussed above with respect to the nano-fingers 104. According to an example, the base sections 504 comprise widths that are subwavelength of light.

When the ridge sections 502 are brought into substantial contact with each other in any of the manners discussed above, an analyte molecule 220 may substantially be trapped between the ridge sections 502 (free ends 106) of the nano-structures 104. Active material layers 506 are also depicted as covering each of the ridge sections 502. In this regard, as excitation light 206 is propagated through the ridge sections 502 as denoted by the arrows 208, hot spots for the emission of Raman scattered light by the analyte molecule 220 may be formed by the evanescent waves (not shown) generated from the excitation light 206. Moreover, the ridge sections 502 may be implemented in the collection of the Raman scattered light emitted from the analyte molecule 220 as discussed above.

Although the apparatus 500 has been depicted as having particular structural characteristics, it should be understood that various modifications to those structural characteristics may be made without departing from a scope of the apparatus 500. For instance, each of the nano-structures 104 may have inverted "L" or other shaped cross-sections instead of the "T" shaped cross-sections depicted in FIG. 5. In addition, or alternatively, although the active layers 506 have been depicted as forming continuous layers over the ridge sections 502, the active layers 506 may instead comprise a non-continuous layer to thereby form sections of active portions along the ridge sections 502.

Figure 6:
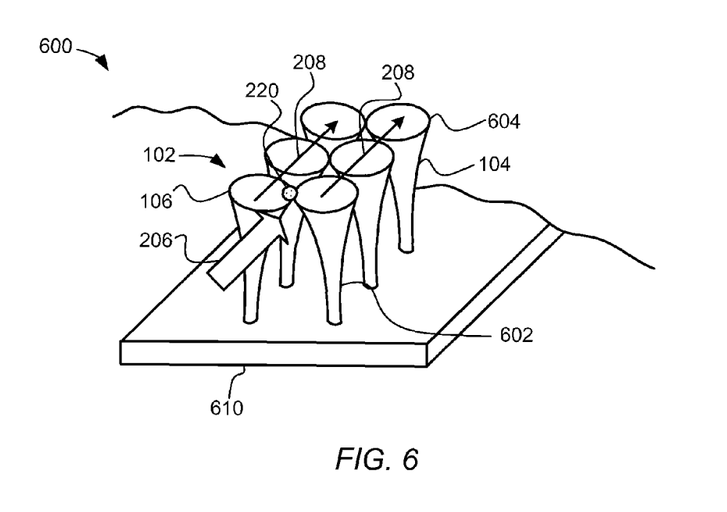

With reference now to FIG. 6, the apparatus 600 includes optical waveguides 102 and nano-structures 104 supported on a substrate 610, which may be equivalent to any of the substrates discussed above. The apparatus 600 is similar to the apparatus 500 depicted in FIG. 5 in that the optical waveguides 102 are integrated into the nano-structures 104.

More particularly, the nano-structures 104 comprise respective pillars having flexible base sections 602 and enlarged ridge sections 604 at the free ends 106 of the nano-structures 104. The base sections 602 and the ridge sections 604 may be formed of the same materials as those discussed above with respect to the optical waveguide 102 to thereby enable excitation light 206 to propagate therethrough. In addition, the base sections 602 and the ridge sections 604 may be formed using any of the fabrication techniques discussed above with respect to the nano-fingers 104 to provide sufficient flexibility in the base sections 602 to enable the nano-structures 104 to be movable between the first and second positions. According to an example, the base sections 602 comprise widths that are subwavelength of light.

When the ridge sections 604 are brought into substantial contact with each other in any of the manners discussed above, an analyte molecule 220 may substantially be trapped between the ridge sections 604 (free ends 106) of the nano-structures 104. Active material layers (not shown) may also be provided on the ridge sections 604. In this regard, as excitation light 206 is propagated through the ridge sections 604 as denoted by the arrows 208, Raman hot spots for the detection of the Raman scattered light emitted by the analyte molecule 220 may be formed by the evanescent waves (not shown) generated from the excitation light 206. Moreover, the ridge sections 604 may be implemented in the collection of the Raman scattered light emitted from the analyte molecule 220 as discussed above.

The enlarged ridge sections 604 collectively provide a substantially high effective refractive index. Because the nano-structures 104 are relatively wider at their free ends 106, the average refractive index of the nano-structures 104, which is a function of the height of the nano-structures 104 above the substrate 610, averaging over this small-scale structure, the effective index is increased as compared to a nano-structure having a uniform cross section. However, as the size of the ridge sections 604 increases, scattering losses increase correspondingly. The gains from the ridge sections 604 may eventually be overwhelmed by the scattering losses, however, these scattering losses may substantially be suppressed by making the nano-structures 104 periodic.

Figure 7:
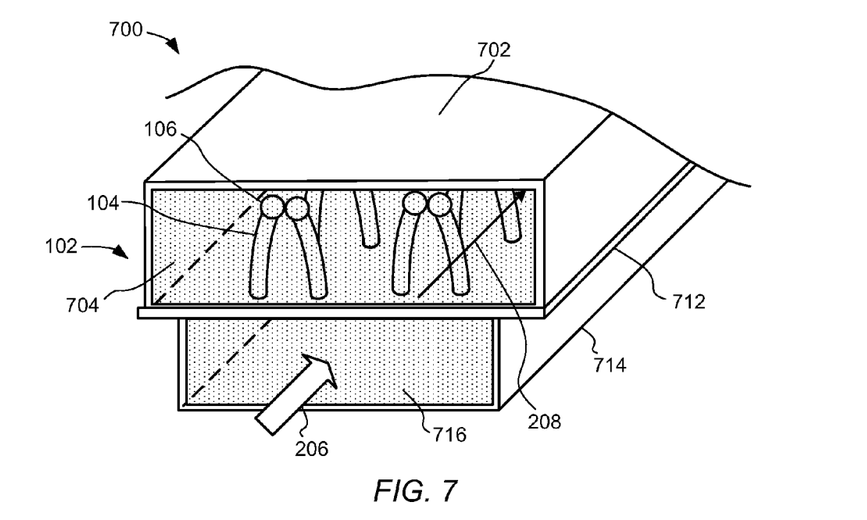

With reference now to FIG. 7, the apparatus 700 includes an optical waveguide 102 and a plurality of nano-structures 104, in this example, nano-fingers. The nano-structures 104 are depicted as being positioned on the optical waveguide, in which the optical waveguide 102 is formed, for instance, of a membrane 712, which may comprise a relatively thin polymer layer, suspended over a housing section 714. As also shown in FIG. 7, a liquid 716, such as water, is contained in a space formed in the housing section 714. In addition, the nano-structures 104 are depicted as being housed within an enclosure 702, within which a liquid 704, such as water, is contained. According to an example, the liquids 704 and 716 have the same refractive index level and thus, may comprise the same type of liquid.

In the example depicted in FIG. 7, a liquid containing the analyte molecule 220 to be tested may initially be introduced into the space provided by the enclosure 702 while the nano-fingers 104 are in the first, spaced, position. In addition, the liquid may be dried to cause the free ends 106 of at least some of the nano-fingers 104 to be in substantial contact with each other as discussed above, to cause the nano-fingers 104 to be in the second position. The liquid 704 may then be introduced into the space provided by the enclosure 702.

The liquid 716 contained in the housing section 714 may form an optical waveguide through which excitation light 206 may be propagated as denoted by the arrow 208. Similarly to the optical waveguides 102 discussed above, the light waves 208 may be TM-polarized and may generate evanescent waves 210 (not shown) that may be emitted through the membrane 712 and onto an analyte molecule 220 located on or between the second ends 106 of at least two nano-fingers 104. The membrane 712 may have a thickness in the range of about 100 nanometers to about 2 microns. By making the polymer layer 712 sufficiently thin, an evanescent field that extends relatively far (for instance a few microns) outside of the membrane 712 may be generated in instances in which the excitation light 208 is directed through the liquid 716. This occurs because the decay length for the evanescent field increases in the liquid 704. In one regard, the nano-fingers 104 may be made longer because of the increased effect of the evanescent field.

The membrane 712 may serve as a low-index-contrast waveguide that is symmetric, except for the nano-fingers 104. As discussed above with respect to FIG. 2, the evanescent waves 210 may cause Raman scattered light to be emitted from the analyte molecule 220. In addition, the emission of the Raman scattered light from the analyte molecule 220 may be enhanced through use of the active material layer 110/nano-particles 112 provided on the free ends 106 or by the material forming the nano-fingers 104 themselves. Moreover, the optical waveguide 102 may be implemented in the collection of the Raman scattered light emitted from the analyte molecule 220 as discussed above.

Figure 8:
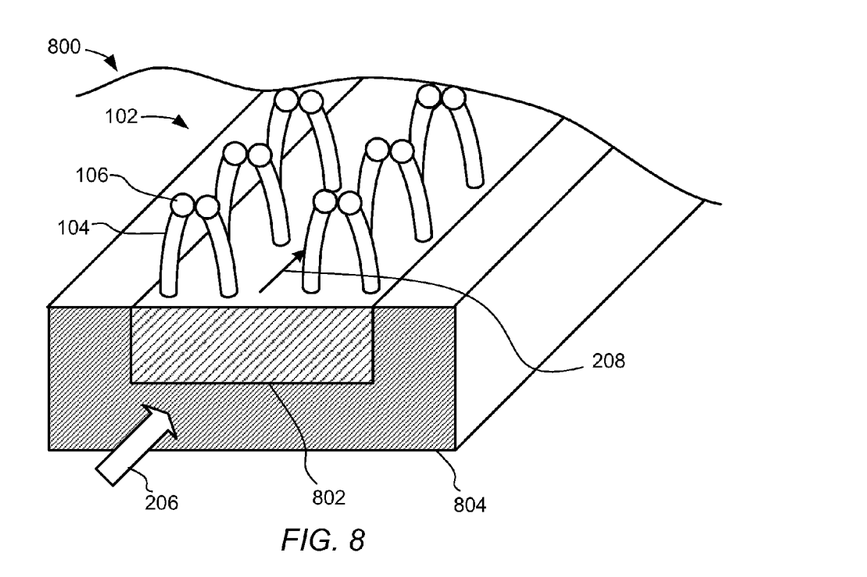

With reference now to FIG. 8, the apparatus 800 includes an optical waveguide 102 and a plurality of nano-structures 104, in this example, nano-fingers. The optical waveguide 102 is depicted as being formed of a first section 802 and a second section 804. The nano-structures 104 are depicted as being positioned on the first section 802 and the second section 804 is depicted as substantially surrounding the first section 802 except for the top portion of the first section 802. The first section 802 and the second section 804 have different refractive indexes. By way of example in which the second section 804 has a refractive index (n), the first section 802 has a slightly higher refractive index (n+Δn). According to particular example, $$\frac{\Delta n}{n} \ll 1.$$

In addition, or alternatively, Δn/n may be in the range of $10^{-3}$ and $10^{-4}$, which may substantially enhance the evanescent field generated by excitation light 206 propagated through the first section 802 as indicated by the arrow 208.

The difference in refractive index between the first section 802 and the second section 804 may be made using lithography processes, laser lighting to locally change an index of refractive of materials such as glass, and by any other suitable process. Because the contrast in the refractive index of the first section 802 and the second section 804 is slight, a relatively larger evanescent field at the position of the nano-structures 104 may be generated when the excitation light 206 is directed through the first section 802.

Figure 9:
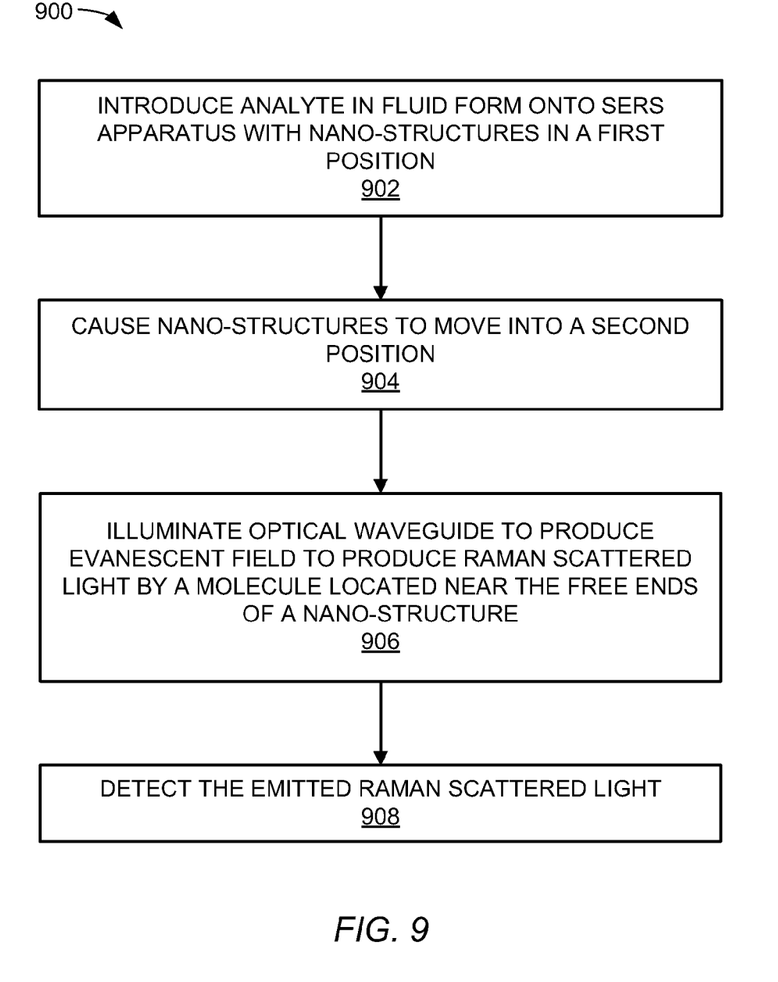
FIG. 9 shows a flow diagram of a method for performing SERS to detect an analyte molecule using a SERS system, according to an example of the present disclosure.

Turning now to FIG. 9, there is shown a flow diagram of a method 900 for performing surface enhanced Raman spectroscopy (SERS) to detect an analyte molecule 220 using a SERS system, according to an example. It should be understood that the method 900 depicted in FIG. 9 may include additional processes and that some of the processes described herein may be removed and/or modified without departing from a scope of the method 900. In addition, although particular reference is made herein to the SERS system 200 in implementing the method 900, it should be understood that the method 900 may be implemented through use of a differently configured SERS system without departing from a scope of the method 900.

At block 902, with the nano-structures 104 in a first position, an analyte containing an analyte molecule 220 to be detected is introduced onto the apparatus 100. Thus, for instance, gaps may be present between the free ends 106 of adjacent ones of the nano-structures 104, in which the gaps are sufficiently large to enable the analyte molecule 220 to fit between the free ends 106.

At block 904, the nano-structures 104 are caused to move into a second position, in which the free ends 106 of at least two of the nano-structures 104 are in substantially close contact with each other to substantially trap an analyte molecule 220 between the free ends 106. As discussed above, and according to an example, the free ends 106 of at least two of the nano-structures 104 may be caused to come into substantial contact with each other through capillary forces acting on the free ends 106 as the fluid analyte evaporates.

At block 906, the optical waveguide 104 is illuminated, for instance, by an illumination source 202. As discussed above with respect to FIG. 2, an excitation light 206 emitted into the optical waveguide 104 is propagated as a wave 208 through the optical waveguide 104. The wave 208 generates evanescent waves 210 that generally cause an analyte molecule 220 located near a free end 106 of a nano-structure 104 to emit Raman scattered light. The emission of the Raman scattered light may be enhanced if the analyte molecule 220 is located near the free ends 106 of multiple nano-structures 104, such as may occur when the analyte molecule 220 is trapped between the free ends 106 when the nano-structures 104 move from the first position to the second position. The emission of the Raman scattered light may also be enhanced if the analyte molecule 220 is positioned near Raman active materials as also discussed above.

At block 908, the detector 204 detects the Raman scattered light, if any, produced from the analyte molecule 220. The Raman scattered light may be detected using free space optics or through the Raman scattered light being generated in the optical waveguide 102 as discussed above with respect to FIG. 2. As discussed above, the detected Raman scattered light may be processed to identify the analyte molecule 220.

According to an example, the method 900 may end following detection of the Raman scattered light at block 908. According to another example, however, blocks 902-908 of the method 900 may be performed over a number of cycles to further enhance the likelihood of detecting sufficiently strong signals to accurately identify the molecules 220 contained in the analyte.

Figure 10:
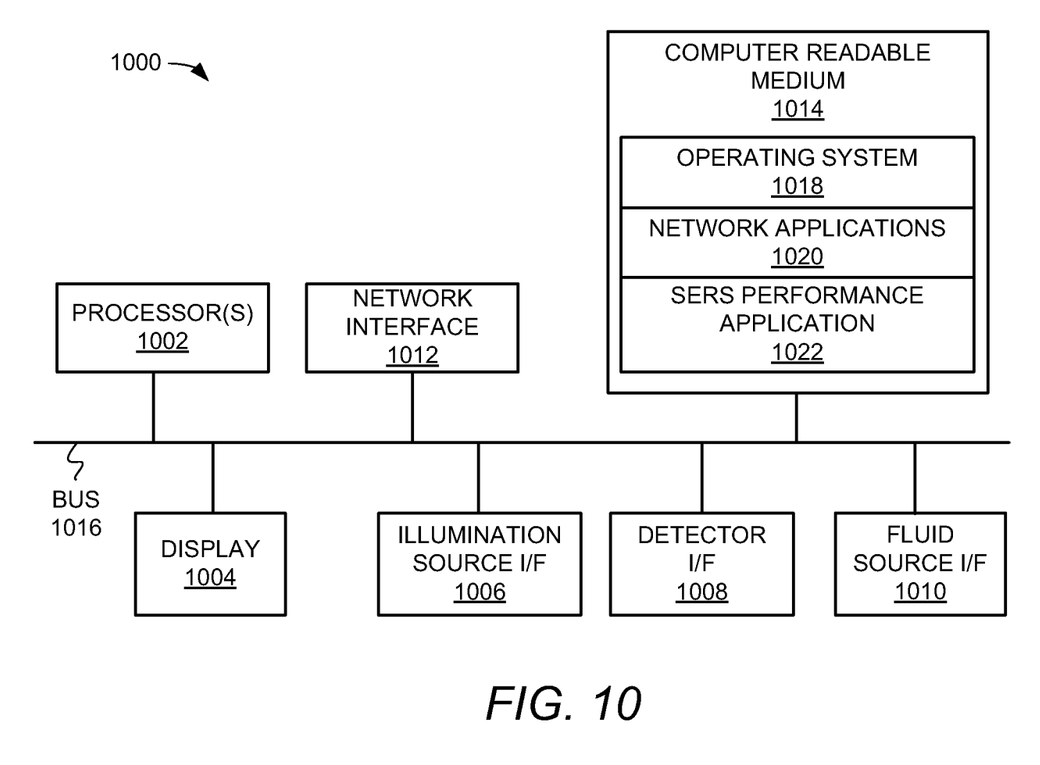
FIG. 10 shows a schematic representation of a computing device to implement or execute the method depicted in FIG. 9, according to an example of the present disclosure.

Turning now to FIG. 10, there is shown a schematic representation of a computing device 1000 to implement or execute the method 900, according to an example. The computing device 1000 includes a processor 1002, such as a central processing unit; a display device 1004, such as a monitor; an illumination source interface 1006; a detector interface 1008; a fluid source interface 1010; a network interface 1012, such as a Local Area Network LAN, a wireless 802.11x LAN, a 3G mobile WAN or a WiMax WAN; and a computer-readable medium 1014. Each of these components is operatively coupled to a bus 1016. For example, the bus 1016 may be an EISA, a PCI, a USB, a FireWire, a NuBus, or a PDS.

The computer readable medium 1014 may be any suitable non-transitory medium that participates in providing instructions to the processor 1002 for execution. For example, the computer readable medium 1014 may be non-volatile media, such as an optical or a magnetic disk; volatile media, such as memory; and transmission media, such as coaxial cables, copper wire, and fiber optics.

The computer-readable medium 1010 may also store an operating system 1018, such as Mac OS, MS Windows, Unix, or Linux; network applications 1020; and SERS performance application 1022. The operating system 1018 may be multi-user, multiprocessing, multitasking, multithreading, real-time and the like. The operating system 1018 may also perform basic tasks such as recognizing input from input devices, such as a keyboard or a keypad; sending output to the display 1004; keeping track of files and directories on the computer readable medium 1010; controlling peripheral devices, such as disk drives, printers, image capture device; and managing traffic on the bus 1016. The network applications 1020 include various components for establishing and maintaining network connections, such as machine readable instructions for implementing communication protocols including TCP/IP, HTTP, Ethernet, USB, and FireWire.

The SERS performance application 1022 provides various software components for implementing a SERS apparatus to detect analyte molecules 220, as described above. In certain examples, some or all of the processes performed by the SERS performance application 1022 may be integrated into the operating system 1018. In certain examples, the processes may be at least partially implemented in digital electronic circuitry, or in computer hardware, machine readable instructions (including firmware and/or software), or in any combination thereof.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing surface enhanced Raman spectroscopy (SERS), said apparatus comprising:
   an optical waveguide that is to propagate light along a first axis, wherein an evanescent field outside of the optical waveguide is to be generated as the light is propagated through the optical waveguide;
   a plurality of flexible nano-structures that extend generally perpendicularly with respect to the first axis, wherein the plurality of nano-structures have respective free ends positioned to be within the evanescent field generated by the light propagated through the optical waveguide; and
   wherein the plurality of nano-structures are movable from a first position and a second position, wherein in the first position, the free ends of the plurality of nano-structures are substantially spaced from each other and in the second position, the free ends of a plurality of the nano-structures are substantially in contact with each other; and
   wherein the plurality of flexible nano-structures comprise a base section supporting a ridge section, wherein a width of the ridge section is substantially larger than a width of the base section, and wherein the ridge section comprises the optical waveguide.

2. The apparatus according to claim 1, wherein the base section comprises a width that is subwavelength of light.

3. The apparatus according to claim 1, wherein the ridge section tapers from the base section.

4. The apparatus according to claim 3, wherein the ridge sections have relatively flat top sections.

5. The apparatus according to claim 1, wherein the plurality of nano-structures are formed of at least one of a polymer material, a metallic material, and a semiconductor material.

6. The apparatus according to claim 1, further comprising:
active material layers disposed on the free ends of the nano-structures, wherein the active material layers comprise Raman-active material layers to enhance Raman light emission from an analyte molecule disposed at least one of on and near the Raman-active material layers.

7. A surface enhanced Raman spectroscopy (SERS) system comprising:
an apparatus for performing SERS, said apparatus comprising:
an optical waveguide that is to propagate light along a first axis, wherein an evanescent field outside of the optical waveguide is to be generated by the light as the light is propagated through the optical waveguide;
a plurality of flexible nano-structures that extend generally perpendicularly with respect to the first axis, wherein the plurality of nano-structures have respective free ends positioned to be within the evanescent field generated by the light propagated through the optical waveguide, wherein the plurality of nano-structures are movable from a first position and a second position, wherein in the first position, the free ends of the plurality of nano-structures are substantially spaced from each other and in the second position, the free ends of a plurality of the nano-structures are substantially in contact with each other, wherein the plurality of flexible nano-structures comprise a base section supporting a ridge section, wherein a width of the ridge section is substantially larger than a width of the base section, and wherein the ridge section comprises the optical waveguide;
an illumination source to illuminate the optical waveguide to cause light to be propagated along the first axis and produce the evanescent field, wherein the evanescent field is to cause Raman scattered light to be emitted from an analyte molecule located near the free end of at least one nano-structure; and
a detector to detect the Raman scattered light emitted from the analyte molecule.

8. The SERS system according to claim 7, wherein the optical waveguide is directly coupled to an optical fiber.

9. The SERS system according to claim 7, wherein the apparatus for performing SERS, the illumination source, and the detector are integrated into a single chip.

10. A method for performing surface enhanced Raman spectroscopy (SERS) to detect an analyte molecule using an apparatus having an optical waveguide and a plurality of flexible nano-structures having free ends positioned to be within an evanescent field to be generated by light emitted through the optical waveguide, wherein the plurality of flexible nano-structures comprise a base section supporting a ridge section, wherein a width of the ridge section is substantially larger than a width of the base section, and wherein the ridge section comprises the optical waveguide, said method comprising:
introducing an analyte in fluid form onto the apparatus while the plurality of flexible nano-structures are in a first position in which gaps are present between the free ends of a plurality of the flexible nano-structures;
causing the plurality of flexible nano-structures to move into a second position in which the free ends on a plurality of the nano-structures to substantially contact each other;
illuminating the optical waveguide to cause light to propagate through the optical waveguide along a first axis and produce an evanescent field outside of the optical waveguide, wherein the plurality of flexible nano-structures extend generally perpendicularly with respect to the first axis, wherein the evanescent field is to cause Raman scattered light to be emitted from an analyte molecule located near a free end of a at least one of the nano-structures; and
detecting the Raman scattered light emitted from the analyte molecule.

11. The method according to claim 10, wherein causing the plurality of flexible nano-structures to move into the second position further comprises causing the plurality of flexible nano-structures to move into the second position by substantially drying the fluid containing the analyte molecule, wherein drying of the fluid causes the free ends of a plurality of flexible nano-structures to come into substantial contact with each other.

12. The method according to claim 10, wherein a portion of the Raman scattered light is emitted into the optical waveguide, and wherein detecting the emitted Raman scattered light further comprises detecting the Raman scattered light emitted into and propagated through the optical waveguide.

* * * * *